(12) United States Patent
Benita et al.

(10) Patent No.: US 7,004,171 B2
(45) Date of Patent: Feb. 28, 2006

(54) SYSTEM FOR TRANSVAGINAL DRUG DELIVERY

(75) Inventors: Simon Benita, Jerusalem (IL); Ram Kluger, Pardessea (IL); Theodor Stern, Jerusalem (IL)

(73) Assignees: Hi-Gienic Intra Vaginal Technologies Ltd., Ceasarea (IL); Yissum Research Development Company of the Hebrew University of Jerusalem, Jerusalem (IL)

( * ) Notice: Subject to any disclaimer, the term of this patent is extended or adjusted under 35 U.S.C. 154(b) by 508 days.

(21) Appl. No.: 10/082,819

(22) Filed: Feb. 25, 2002

(65) Prior Publication Data

US 2003/0163103 A1 Aug. 28, 2003

(51) Int. Cl.
*A61F 6/06* (2006.01)
(52) U.S. Cl. ..................... 128/830; 128/832
(58) Field of Classification Search ......... 128/830–841
See application file for complete search history.

(56) References Cited

U.S. PATENT DOCUMENTS

| | | | |
|---|---|---|---|
| 3,918,452 A | 11/1975 | Cornfeld | 128/270 |
| 3,993,073 A * | 11/1976 | Zaffaroni | 424/424 |
| 4,077,407 A * | 3/1978 | Theeuwes et al. | 424/427 |
| 4,256,108 A * | 3/1981 | Theeuwes | 424/424 |
| 4,309,997 A | 1/1982 | Donald | 128/270 |
| 4,340,055 A | 7/1982 | Sneider | 128/270 |
| 5,201,326 A | 4/1993 | Kubicki et al. | 128/832 |
| 5,417,224 A | 5/1995 | Petrus et al. | 128/833 |
| 6,086,909 A | 7/2000 | Harrison et al. | 424/430 |
| 6,197,327 B1 | 3/2001 | Harrison et al. | 424/430 |
| 6,328,991 B1 * | 12/2001 | Myhling | 424/430 |

FOREIGN PATENT DOCUMENTS

WO   WO 02/17981   3/2002

OTHER PUBLICATIONS

Woolfson et al., "Drug Delivery by the Intravaginal Route", Critical Reviews in Therapeutic Drug Carrier Systems 17:509-555, 2000.

* cited by examiner

*Primary Examiner*—Michael Anthony Brown
(74) *Attorney, Agent, or Firm*—Fish & Richardson P.C.

(57) ABSTRACT

A transvaginal drug delivery system comprising: (a) a deposition comprising an effective amount of said drug and, optionally, a wetting agent; and (b) a polymeric support on which said deposition is deposited. Also disclosed is a catamenial tampon for insertion in a human vagina comprising: (a) an inner core comprising an absorbent material; (b) an outer layer comprising a liquid-permeable material; and (c) a delivery system according to the invention. A method of transvaginal drug delivery is also described.

8 Claims, 7 Drawing Sheets

SYSTEM FOR TRANSVAGINAL DRUG DELIVERY

FIELD OF THE INVENTION

This invention relates to a system and method for transvaginal drug delivery.

BACKGROUND OF THE INVENTION

Transvaginal drug delivery is a well known means of administering drugs to a female (Woolfson, A. D., Malcolm, R. K. and Gallagher, R. (2000) *Critical Reviews in Therapeutic Drug Carrier Systems* 17:509–555). The transvaginal route has several advantages: (1) it is non-invasive; (2) the vagina consists of highly perfused tissue with a well-developed blood supply; (3) it avoids first-pass metabolism in the liver. The transvaginal route may be used both for local drug treatment as well as systemic drug absorption.

Transvaginal drug delivery systems may be classified in two main groups: those adapted from semisolid topical systems and those designed specifically for intravaginal use. Known systems include the following:

Mucoadhesive gels and hydrogels. These are weakly crosslinked polymers which are able to swell in contact with water and spread onto the surface of mucus. These have been used for cervical ripening, spermicidal contraception, vaccination and treatment of vaginal infections;

Vaginal tablets. They may be formulated with mucoadhesive polymers in order to increase intravaginal residence time. They have been used for cervical ripening, spermicidal contraception, pregnancy termination, analgesia and urge incontinence;

Vaginal pessaries and suppositories. These are substances such as natural gums, fatty acids, alum and rock salts which were originally used by the ancient Egyptians as contraceptives. They have been used for cervical ripening, treatment of vaginal infections, pregnancy termination and progesterone therapy;

Microspheres for the delivery of peptide and protein drugs;

Intravaginal rings. These are torus-shaped polymeric devices designed to release one or more incorporated drugs in a controlled fashion. They have been used for steroidal and spermicidal contraception, and estrogen replacement therapy.

U.S. Pat. No. 3,918,452 (Cornfeld) discloses vaginal sponges and/or tampons impregnated with contraceptive compositions. The composition comprises microcapsules containing a contraceptive drug and which provide sustained release of the drug before, during and/or after coitus.

U.S. Pat. No. 4,309,997 (Donald) discloses a medicated tampon in the form of a soft, porous foam ball of spherical configuration. The tampon is as impregnated with a contraceptive drug and/or an antibiotic for control of venereal disease. The tampon is inserted into the vagina to cover the cervical area while permitting intercourse to take place.

U.S. Pat. No. 5,201,326 (Kabicki et al) discloses a rod-shaped medical tampon for releasing an active substance. The tampon includes a core of compressed fibers an a cover surrounding the core and glued thereto, the cover comprising hardened collagen foam or hardened gelatin foam impregnated with a retardant, such as a fatty substance, including the dissolved active substance to be released. The active substance may be antibiotics, sulfonamides, antimycotics, fungicides or hormones. U.S. Pat. No. 5,417,224 (Petus et al) discloses a tampon comprising a porous spherical member having an inner region configured radially within an outer region, a cord extending through a passage extending through the spherical member, a spermicide within the pores of the inner region and a lubricant within the pores of the outer region.

U.S. Pat. No. 6,086,909 (Harrison et al) discloses devices and methods for the treatment of dysmenorrhea which comprise an intravaginal drug delivery system containing an appropriate pharmaceutical agent which is released into the vagina and absorbed through the vaginal mucosa via lymphatic and venous channels to the uterus. The drug delivery system may include a tampon device, vaginal ring, pessary, tablet, vaginal suppository, vaginal sponge, bioadhesive tablets, bioadhesive microparticle, cream, lotion, foam, ointment, solution or gel. The system may additionally include a muco-adhesive agent and/or a penetration enhancer. In the case where the device is an absorbent vaginal tampon, one end of the tampon has a means for delivering the pharmaceutical agent while the other end has means for conveying fluid discharged from the uterus (such as menses fluid) to the tampon, thereby preventing contact of the fluid with the agent.

Non-steroidal anti-inflammatory drugs (NSAID) are marketed worldwide as over the counter (OTC) analgesics and antipyretics, of which, the most commonly used are aminophen, aspirin, ibuprofen and naproxen.

The mechanism of most anti-inflammatory, antipyretic and analgesic effects of NSAIDs result from the inhibition of prostaglandin synthesis from arachidonic acid. The target of NSAID action is PGHS, which is the key rate-limiting enzyme in the production of prostanoids. This enzyme catalyzes the conversion of arachidonic acid to $PGH_2$ via a two-step reaction mechanism involving sequential cyclooxygenase and peroxydase activities.

Generally, OTC analgesics are regarded as safe for the majority of patients. However, adverse effects have been reported and are mainly associated with the oral administration of NSAIDs, occurring mostly in the gastrointestinal tract. Dyspepsia appears to be the most common side effect, but serious adverse effects such as bleeding, ulceration and perforation can also occur. The potential of adverse renal effects have also been reported, although for some NSAIDs this relationship remains controversial. Most adverse renal effects, however, are reversible on prompt discontinuation of the analgesics.

Numerous studies have dealt with the controlled release of NSAIDs from capsules, matrices, or gels. Colloidal liposomal carriers in an injectable 25% poloxamer gel were used to investigate the release properties of ibuprofen. Poloxamer gel was also used for the epidural injection of lidocaine and ibuprofen. Biodegradable matrices such as poly lactic acid (PLA) were also used for the controlled release of analgesics. Gel-yielding egg albumin-based matrices were used to study drug release kinetics. Other sustained release formulations consisted of hydroxpropyl methylcellulose (HPMC) matrices or matrices of synthetic crosslinked polymeric resins, as for example crosslinked poly acrylic acid.

It is estimated that 30 to 50% of the women of childbearing age in the US, are affected by painful menstrual periods or dysmenorrhea and 10 to 15% of those women are incapacitated for 1 to 3 days each month. The chief symptom that women experience is spasmodic pain of the lower abdomen, which may radiate to the back and along the thighs.

The etiology of these symptoms has been determined to be related to the pharmacologic actions of prostaglandin E2(PGE2) and prostaglandin F2α (PGF2α), which are formed from phospholipids of dead cell membranes in the menstruating uterus. PGE2 causes disaggregation of platelets and is a vasodilator, whereas PGF2α mediates or potentiates pain sensations and stimulates smooth muscle contraction.

NSAIDs are successful as analgesics in 77 to 80% of dysmenorrhea patients, ibuprofen, naproxen, or naproxen sodium being the usual initial choices.

SUMMARY OF THE INVENTION

It is an object of the invention to provide a novel delivery system for use with a feminine hygienic product, such as a tampon, to deliver a drug through the female vagina.

It is another object of the invention to provide a method of transvaginal drug delivery.

In a first aspect of the invention, there is provided a transvaginal drug delivery system comprising:
  (a) a deposition comprising an effective amount of the drug and, optionally, a wetting agent; and
  (b) a polymeric support on which the deposition is deposited.

In the present specification, the term "transvaginal" includes both local delivery to the vagina (intravaginal) as well as through the vagina to other target tissues in the body, including systemic effects.

The drug used in the delivery system of the invention may be any drug which either is released and acts locally or which is absorbed through the vaginal mucosa to other locations in the body. Examples of such drugs include non-steroidal anti-inflammatory drugs (NSAID), anti-prostaglandins, prostaglandin inhibitors, COX-2 inhibitors, local anaesthetics, calcium channel blockers, potassium channel blockers, β-adrenergic agonists, leukotriene blocking drugs, smooth muscle inhibitors, vasodilators, hormone replacement drugs, androgenic hormones and drugs capable of inhibiting dyskinetic muscle contraction.

Non-limiting examples of NSAIDs suitable for use in the method of the invention include Aspirin, Ibuprofen, Indomethacin, Phenylbutazone, Bromfenac, Fenamate, Sulindac, Nabumetone, Ketorolac, and Naproxen. Examples of local anesthetics include Lidocaine, Mepivacaine, Etidocaine, Bupivacaine, 2-Chloroprocaine hydrochloride, Procaine, and Tetracaine hydrochloride. Examples of calcium channel antagonists include Diltiazem, Israpidien, Nimodipine, Felodipine, Verapamil, Nifedipine, Nicardipine, and Bepridil. Examples of potassium channel blockers include Defetilide, E-4031, Almokalant, Sematilide, Ambasilide, Azimilide, Tedisamil, RP58866, sotalol, Piroxicam, and Ibutilide. Examples of β-adrenergic agonists include Terbutaline, Salbutamol, Metaproterenol, and Ritodrine. Vasodilators, which are believed to relieve muscle spasm in the uterine muscle, include nitroglycerin, isosorbide dinitrate and isosorbide mononitrate. Examples of COX-2 inhibitors are Celecoxib, Meloxicam and Flosulide. Examples of hormone replacement drugs are estrogen or estradiol and progestogen. Examples of androgenic hormones are testosterone and other androgenic hormones.

The drug may be present in the system in combination with a biocompatible excipient or carrier acceptable for application of the drug to the vaginal epithelium. Although the mechanism may be diffusion-controlled, the co-inclusion of excipients such as wetting agents or surfactants in the formulation, may be necessary. The term "an effective amount" in this specification means an amount sufficient to attain a therapeutically effective amount of the drug in the target tissue or system. In a preferred embodiment, the drug is absorbable through the vaginal mucosa and thereby transmitted via venous and lymphatic channels to the uterus or to the general blood circulation.

The deposited drug or drug composition may include any polymer capable of producing and facilitating a coherent deposition on the polymeric support material. Such polymers include but are not limited to polyesters, olefins, cellulose and cellulose derivatives, PVA and PVP.

The polymeric support may be any polymeric material capable of serving as a support for the deposited material, and includes non-woven as well as woven materials. Examples of such support material include polypropylene, polyethylene, cellulose and cellulose derivatives or any other polymer which can be processed as a fiber.

A preferred shape of the polymeric support is a rectangular strip, which preferably consists of one or more layers, for example, 2–16 layers. Other shapes for the strip are also contemplated as part of the invention.

Examples of wetting agents which may be used in the drug delivery system of the invention include glycerol, polyethylene glycol (PEG), polypropylene glycol (PPG) and surfactants with an HLB ranging from 10 to 18 such as Tween 80. Preferred wetting agents are glycerol and PEG-8000.

The delivery system of the invention is preferably used together with a catamenial tampon, as will be explained in more detail below.

Preferably, more than one delivery system will be placed in a tampon on different sides, so as to release the drug in all directions.

Among the advantages of using the delivery system of the invention for releasing a drug to the surrounding environment of the female urogenital tract is the contribution both to the economy of the manufacturing process of the tampon as well as to its reproducibility. In addition, the amount of drug necessary to use in the system to obtain a given effect may be significantly less than in systemic methods of drug administration.

In a second aspect of the invention, there is provided catamenial tampon for insertion in a human vagina comprising:
  (a) an inner core comprising an absorbent material;
  (b) an outer layer comprising a liquid-permeable material; and
  (c) a delivery system according to the invention.

One or more of the polymeric supports or strips of the delivery system may be attached to the tampon, as will be described in detail below. Preferably, the delivery system is positioned between the inner core and the outer layer. Optionally, the tampon further comprises a polymeric water-impermeable film behind the strips of the delivery system, e.g. between the delivery system and the inner core. Preferably, the film is comprised of high-density polyethylene (HDPE), In a third aspect of the invention, there is provided a method of transvaginal drug delivery comprising inserting a catamenial tampon into a vagina, wherein the catamenial tampon comprises:
  (a) an inner core comprising an absorbent material;
  (b) an outer layer comprising a liquid-permeable material; and
  (c) a transvaginal drug delivery system according to the invention.

Preferably, the drug is a NSAID such as naproxen or ibuprofen.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF SPECIFIC EMBODIMENTS

I. Delivery System

The delivery system of the invention is composed of a polymeric support, such as a non-woven polymer material, on which a deposition is deposited. The deposition comprises a drug which may be released to the surrounding environment. Examples of such drugs are listed above in the summary of the invention. In one embodiment, the drug is dissolved in a solvent which is applied to the support. The deposition is deposited by evaporation of the solvent The polymeric support is placed near the surface of the tampon. Preferably, the delivery system is positioned between the inner absorbent core of the tampon and its outer covering layer. The polymeric support may be in any geometrical form or shape, Preferably, the support is in the form of rectangular strips of material, although other shapes are also possible. A plurality of these strips may be placed on different sides of the tampon in order to release the drug in all directions. In the following discussion, several non-limiting examples are provided of tampons prepared according to the invention.

EXAMPLE 1

Tampons which undergo both radial and longitudinal expansion are generally manufactured for use with various types of applicator devices. The longitudinal expansion is generally more than 10% of its unexpanded length. This type of tampon comprises an inner core of absorbent material, such as cellulose fibers and/or cotton fibers, enveloped by an outer layer of liquid-permeable material such as a non-woven polymer, as for example polypropylene, polyethylene, polyester, cellulose, cellulose derivatives, or any combination of the above. This type of tampon is referred to in this specification as a "folded-type" tampon.

Figure 1A:
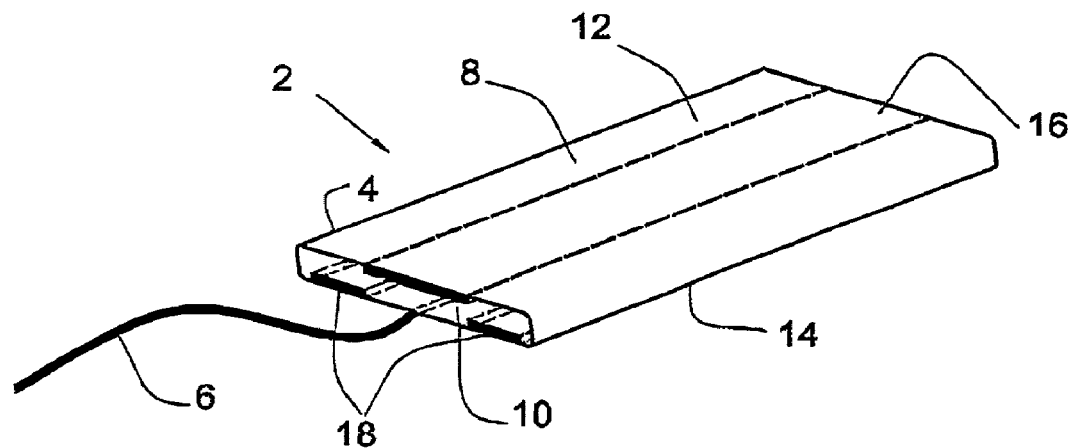
FIGS. 1a and 2a are perspective top views of a folded-type tampon in its flat form with two different embodiments of a delivery system in accordance with the invention.

A folded-type tampon according to one embodiment of the invention is illustrated in FIG. 1a, in which can be seen a tampon 2 in its flat form comprising a body 4 and a withdrawal cord 6. The body 4 of the tampon comprises an outer layer 8 enveloping an inner absorbent core 10. The outer layer is held to the inner core in ways well known in the art, such as sewing or welding. The flat body has an upper 12 and a lower 14 surface.

In this embodiment, a delivery system according to the invention in the form of three rectangular polymeric strips are positioned between the outer layer and the inner core, in parallel to the longitudinal axis of the body. One relatively wide strip 16 is on the upper surface 12 of the body (under the outer layer 8) and two narrow strips 18 are on the lower surface 14. The length of the strips may be approximately equal to the length of the flat body, and preferably equal to it. Preferably, the width of the wide strip is approximately twice the width of the narrow strips. Typical, non-limiting dimensions may be as follows; length and width of flat tampon—5–9.5 and 4–5 cm, respectively; widths of wide and narrow strips—1.5–2.5 cm and 0.7–1.5 cm, respectively.

Figure 1B:
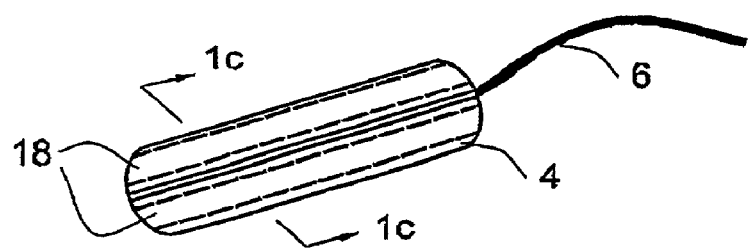
FIGS. 1b and 2b are perspective views of a folded-type tampon in its final folded and pressed form.
Figure 1C:
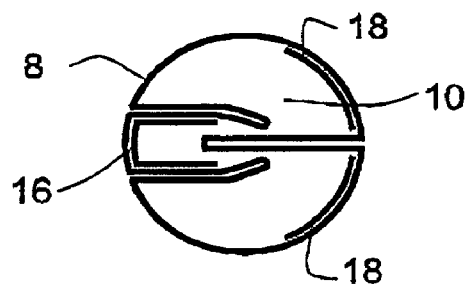
FIGS. 1c and 2c are sectional views along lines 1c—1c and 2c—2c in FIGS. 1b and 2b, respectively.

When the tampon is folded, it is compressed both lengthwise and widthwise to form the conventional tampon shape, as shown in FIG. 1b. The strips 18 are aligned near the outer surface of the body of the tampon. The tampon takes on a W-like shape in cross-section, as illustrated in FIG. 1c, in which can be seen the inner core 10, the outer layer 8 and the wide 16 and narrow 18 strips below the outer layer. It may be seen from the figure that the edges of the wide strip 16 are folded within the folds of the inner core 10, thereby releasing the drug absorbed therein to within the tampon as well as to the surrounding environment.

EXAMPLE 2

Figure 2A:
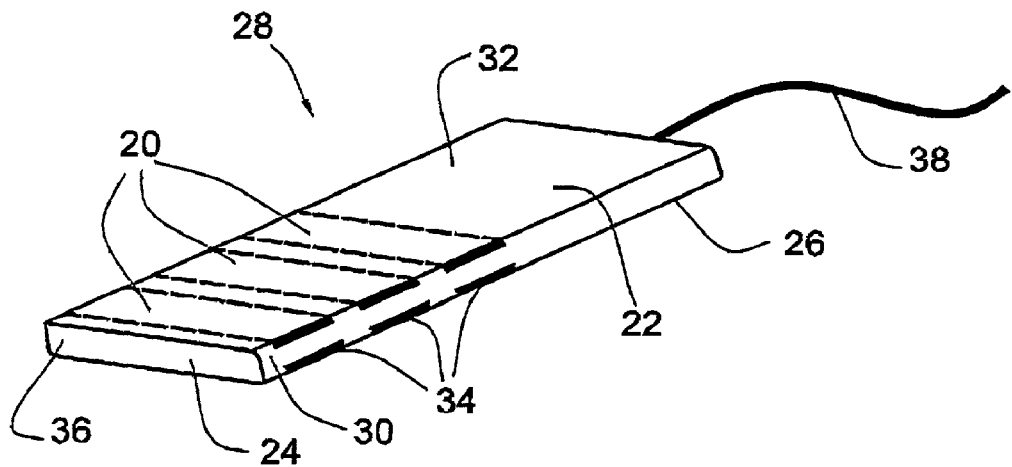

In another embodiment, illustrated in FIG. 2a, three strips are positioned at spaced intervals between the outer layer 22 and the inner core 24 of the flat tampon 28, perpendicularly to the longitudinal axis of the flat body 26 of the tampon. In this embodiment, the strips are wound around the width of the body 26 and then excised at the lateral edges 30 of the body so that there are 3 strips 20 on the upper surface 32 of the body and 3 corresponding strips 34 on the underside of the body. The length of each of the strips is equal to the width of the flat tampon. Preferably, the strips are positioned closer to the front end 36 of the tampon, opposite the withdrawal cord 38, since this the end with which the menstrual fluid first comes into contact.

Figure 2B:
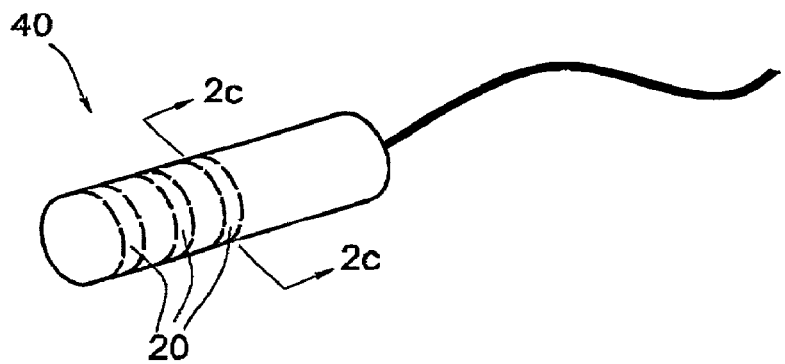
Figure 2C:
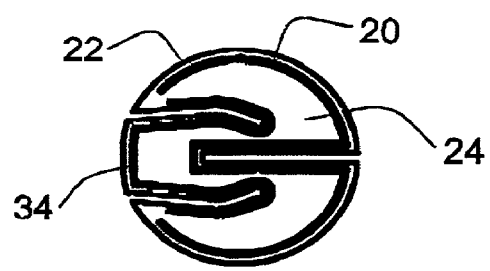

The folded tampon 40 is illustrated in FIG. 2b, in which can be seen the annular strips 20. FIG. 2c shows how the strips 20,34 appear near the outer surface of the tampon between the outer layer 22 and the inner core 24, as well as within the folds of the inner core.

EXAMPLE 3

Figure 3A:
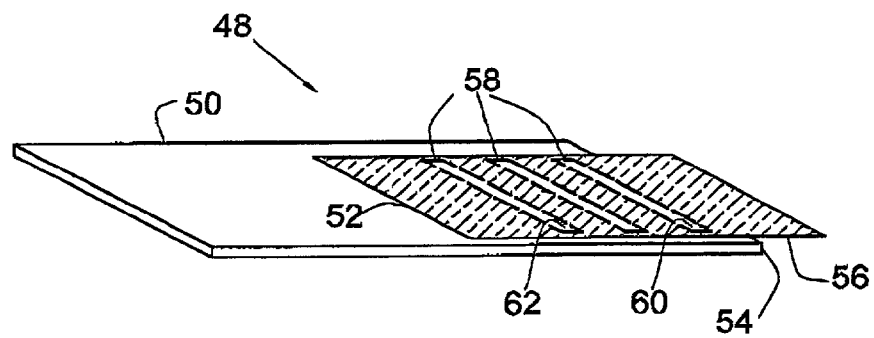
FIGS. 3a and 4a are perspective top views of a rolled-type tampon in its flat form with two different embodiments of a delivery system in accordance with the invention.
Figure 3B:
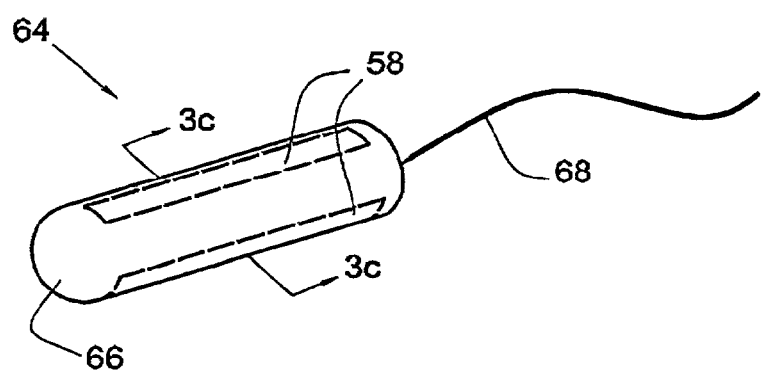
FIGS. 3b and 4b are perspective views of a rolled-type tampon in its final, rolled and pressed form.
Figure 3C:
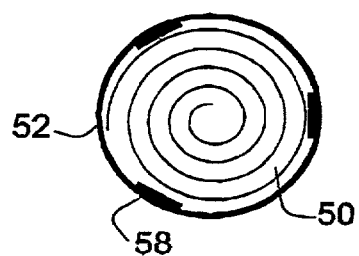
FIGS. 3c and 4c are sectional views along lines 3c—3c and 4c—4c in FIGS. 3b and 4b, respectively.

A typical tampon which undergoes primarily radial expansion (<10% longitudinal expansion, if at all) is referred to in this specification as a "roiled-type" tampon and is shown in FIGS. 3a–3c. As in the folded-type tampon described above, it comprises an inner core of absorbent material, as in Example 1, enveloped by an outer layer of liquid-permeable material, as in Example 1. The rolled-type tampon differs from the folded-type tampon, inter alia, in their dimensions as well as in the manner of forming of the tampon. These differences affect the placement of the strips.

As shown in FIG. 3a, the flat tampon 48 comprises an absorbent layer 50 on which is placed an outer layer 52. The absorbent layer 50 is in the form of an extended rectangular ribbon. The material of the outer layer 52 is generally heat sealed to the upper side of the absorbent layer near one of its ends 54, an extension 56 of the outer layer partly extending beyond the end 54 of the absorbent layer. The length of the extension 56 is substantially equivalent to the circumference of the tampon in its final, folded form.

According to one embodiment of the invention, three parallel spaced rectangular polymeric strips 58 are positioned equidistantly from each other, perpendicular to the longitudinal axis of the outer layer, and between the absorbent layer 50 and the outer layer 52. The ends of the strips are distanced from the longitudinal edges of the outer layer, and the strip 60 closest the end 54 of the absorbent layer is inwardly displaced from that end. The distance from the strip 62 farthest from the end 54 of the absorbent layer to that end is approximately equal to the circumference of the tampon in its folded form.

Typical, non-limiting dimensions of the various tampon components are given below for exemplary purposes only: length, width and thickness of absorbent layer—20–30 cm, 4–6 cm and 0.4–1.0 cm, respectively; length and width of outer layer—5–15 cm and 4–4.5 cm; circumference of tampon—3–4.5 cm; length of strips —3.5–5.5 cm.

FIG. 3b shows the tampon 64 in its folded form comprising the body 66 and withdrawal cord 68. During the forming process, the absorbent layer of the flat tampon (FIG. 3a) is rolled up onto itself along its longitudinal axis towards the end on which the strips and outer layer are placed, and the extension 56 of the outer layer is heat welded to the opposite end of the outer layer, thus enveloping the absorbent layer which now forms the core of the tampon. Two of the three strips 58 may be seen in FIG. 3b through the outer layer, with the third strip out of sight behind the body of the tampon. FIG. 3c shows the three components of the tampon according to the invention: the rolled up inner absorbent core 50, the outer layer 52 and the strips 58.

EXAMPLE 4

Figure 4A:
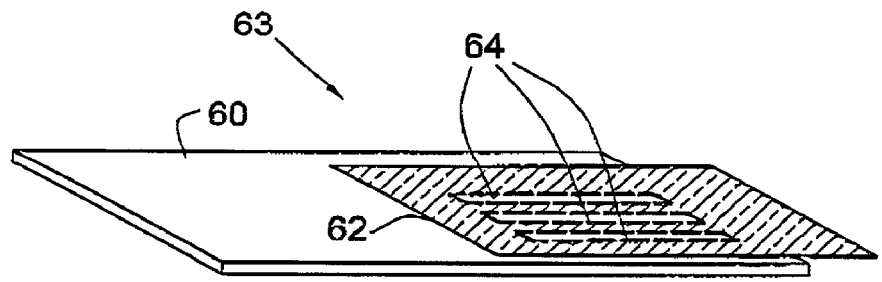
Figure 4B:
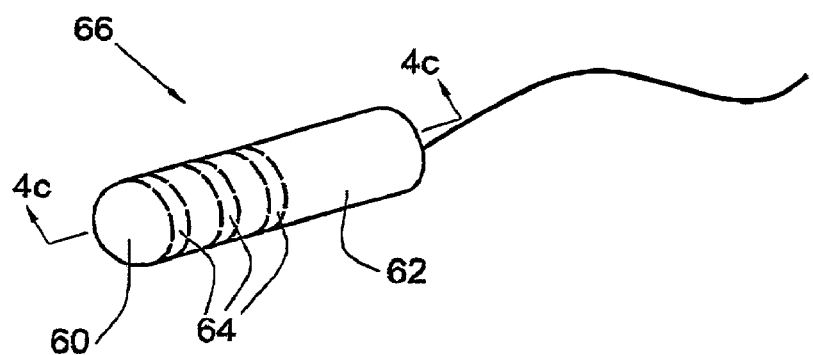
Figure 4C:
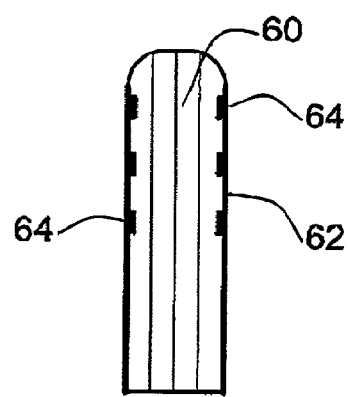

In this embodiment, illustrated in FIGS. 4a–4c, the strips are placed parallel to the longitudinal axis of the outer layer rather than perpendicular thereto. Thus, FIG. 4a illustrates the absorbent layer 60 and outer layer 62 of the flat tampon 63 as in the previous example. Three parallel equidistant strips 64 are placed between the two layers in parallel to the longitudinal axis of the outer layer. The length of each strip is equal to the circumference of the tampon in its final form. Preferably, the strips are placed proximate to the anterior end of the folded tampon.

FIGS. 4b and 4c show the tampon 66 in its folded form comprising the inner core 60, the outer layer 62 and the strips 64.

II. In vitro Experiments

A. Introduction

The following is a summary of the main results and conclusions of in vitro release studies, conducted with two selected NSAIDs, Naproxen and Ibuprofen, using the delivery system of the invention.

Due to the relatively hydrophobic nature of Naproxen and Ibuprofen, special attention should be given to the potential extent of bioavailability of the drugs, from the formulated tampons as a result of the small fluid volume in the vagina during menstruation (5–8 ml). The availability of the drugs is mainly governed by two processes: Vaginal mucosa tissue penetration, which in this case is not considered a limiting factor, and the release pattern of the drugs from the formulated tampons, the dependence of which is mainly affected by drug aqueous solubility and diffusion.

Normally, in the case of in vitro release studies of relatively hydrophobic drugs with good tissue penetration, the experiments are conducted under "SINK conditions". The term SINK conditions originated from the fact that the drug concentration gradient between the external and internal epithelial layer is always maximal, and that the tissue or blood acts as a natural 'sink', i.e. the drug is instantaneously absorbed the moment it dissolves. Therefore, under in vivo conditions, there is no concentration buildup and hence the retarding effect of low and/or moderate concentration gradient in unlikely to occur. In order to simulate the in vivo sink conditions, in vitro dissolution or release kinetics studies are usually conducted using a large volume of dissolution or release medium, so that the solute concentration never reaches more than 5–10% of its maximum solubility under identical experimental conditions. If such conditions are maintained, the low aqueous solubility of the drug does not represent anymore a rate-limiting factor. All in vitro tests in this specification were conducted under sink conditions using 10% of maximum solubility concentration, unless otherwise specified.

B. Materials and Methods

Materials:

Both drugs were kindly provided by Teva Pharmaceuticals, Ltd., Israel, and are of pharmacopoeia grade. All other ingredients used in the study were analytical or HPLC grade.

Methods:

1. Preparation of Delivery System:

Based on previous knowledge, the following formulation was retained: each one of the drugs was first dissolved in ethanol, at a concentration determined by the drug dosage per tampon, and glycerol was added to a percentage of 15% calculated on drug weight basis. Glycerol acts as a wetting agent. The co-inclusion of other wetting agents or surfactants in the formulation may be necessary at times. The formulation was loaded on non-woven (NW) strip (7.5–8.5×2.5 cm) (i.e. the delivery system), by immersing the NW in an ethanol solution, containing the formulation, and eventually evaporating the solvent. Both ethanol and acetone were found suitable for this method, nevertheless, ethanol was chosen due to its significantly lower toxicity.

The formulation-containing strips of the folded-type were folded 2 times around the axial direction and 7.5 cm-long strips were prepared by pressing the folded material at 1 ton/cm$^2$ for 30 seconds. 4 layered strips were obtained by using a single PP/PE (NW). One 2.5 cm strip and two 1.25 cm strips were attached to a tampon in the longitudinal direction as shown in FIG. 1a.

The dose preliminarily chosen, was 50 mg of the drug per tampon and was compared with different lower and higher doses, in terms of release pattern efficiency. For simplicity and clarity reasons, the two drugs chosen for this study are dealt with separately.

2. Release of Ibuprofen: In vitro Release Kinetics Conditions:

SINK Conditions:

The release medium used for these experiments was the Sorensen-Walbum buffer, chosen here due to its lack of absorbance in the UV range, thus causing less interference with the analytical drug detection process. The buffer consisted of glycine (0.1 M) and NaCl (0.1 M), adjusted to pH 7.4 with NaOH (0.1M).

In order to establish SINK conditions, the saturation concentration of Ibuprofen, under the release conditions, was determined. A large excess of Ibuprofen was added to 50 ml of the Sorensen buffer and agitated in a sealed flask at 37° C., for a period of 24 hours The saturation concentration of Ibuprofen under these conditions, as determined by HPLC, was 100 $\mu$g/ml. Accordingly, the SINK conditions concentration was set to 10 $\mu$g/ml. It is worth mentioning that a significantly higher saturation concentration can be reached by first dissolving the drug in a small quantity of ethanol and then mixing it with the buffer solution. Nevertheless, these are not the conditions under which the drug is released in vitro or in vivo.

3. HPLC Method for Ibuprofen Determination:

Ibuprofen concentrations were determined by means of high performance liquid chromatography (HPLC), using the method described in Pharmaceutical Research (1998) 15:482–487.

Column: RP-$C_{18}$, 5 $\mu$m, 25 cm, (Merck) at ambient temperature.

Flow rate: 2 ml/min.

Isocratic mobile phase: acetonitrile: 0.1M sodium acetate (35:65 v/v), adjusted to pH 6.2 with glacial acetic acid.

UV detector at 222 nm.

Detection limit: 0.05 $\mu$g/ml.

The linear relation of peak area to calibration concentrations obtained in a concentration range of 0–2000 $\mu$g/ml was linear and yielded an r value higher than 0.99.

4. Release of Naproxen: In vitro Release Kinetics Conditions

SINK Conditions:

In order to establish sink conditions, the saturation concentration of Naproxen, under the release kinetics experimental conditions, was determined, in the same manner as described before for Ibuprofen. A large excess of Naproxen was added to 50 ml of the Sorensen buffer and agitated in a sealed flask at 37° C., for a period of 24 hours.

The saturation concentration of Naproxen under these conditions, as determined by HPLC, was 109 $\mu$g/ml, only slightly higher than that of Ibuprofen. Accordingly, the sin conditions concentration was set to 10.9 $\mu$g/ml, which is 10% of the saturation conditions.

5. HPLC Method:

Naproxen concentrations were determined by HPLC using the method described in Acta Phanniacol. et Toxicol. (1980) 47:267–273.

Column: RP-$C_{18}$, 5 $\mu$m 25 mm, (Merck) at ambient temperature.

Flow rate: 2 ml/min.

Isocratic mobile phase: acetonitrile: 100 mM aimnonium acetate (40:60 v/v), adjusted to pH 5.5 with glacial acetic acid.

UV detector at 280 nm.

Detection limit: 0.02 $\mu$g/ml.

The linear relation of peak area to calibration concentrations obtained in a concentration range of 0–2000 $\mu$m/ml was linear and yielded an r value higher than 0.99.

Results

1. Fluid Absorption

Formulated tampons (with either ibuprofen or naproxen) were enclosed in a flexible plastic net. The net was firmly tied around the tampons, so that it allowed a maximum absorption of 6 ml of the release medium, which is close to the absorption volume of menstrual fluids under physiological conditions. For comparison purposes, the extent of net tightness was decreased to allow a final absorption volume of 8–10 ml.

Figure 5:
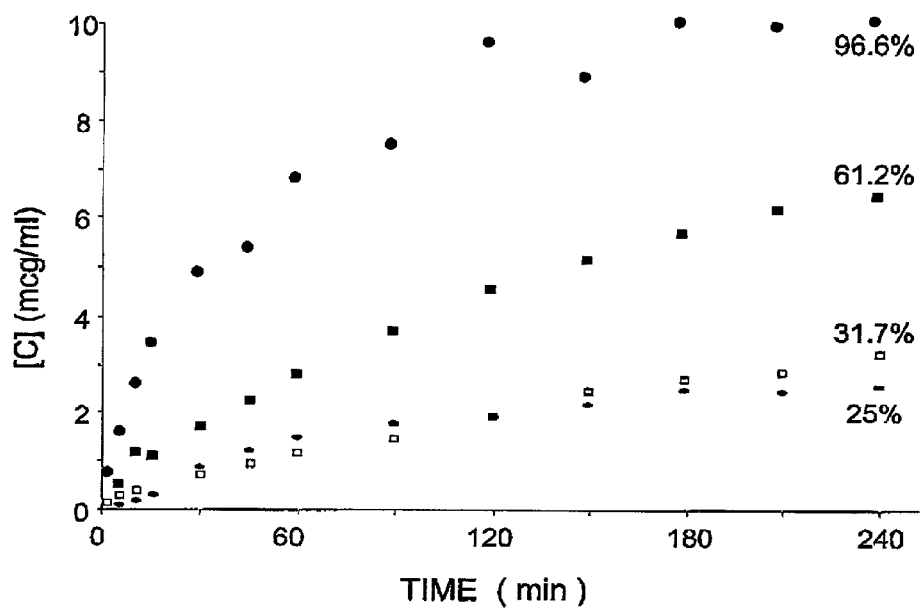
FIG. 5 shows release profiles of formulated tampons containing either 50 mg or 25 mg ibuprofen, in net enclosure permitting different fluid volume absorption (highest release value (%), after 4 hours of incubation, is annotated). ●-50 mg. very loose net, 10 ml; ■-50 mg. loose net, 8.9 ml; □-50 mg. tight net, 6 ml; ◆-25 mg tight net, 6 ml.

FIG. 5 summarizes the ibuprofen release results obtained comparing the effect of two parameters—fluid absorption and amount of formulation—on the drug release profile.

Although some effect of the formulation amount is observed, the most significant factor influencing the release profile is the fluid absorption volume. Increasing the absorption volume from 6 ml to 8.9 ml and finally to 10 ml, led to an increase in drug release from 32% to 61% and to 97%, respectively.

At this stage, it was concluded that the drug release rate from a tampon will markedly depend on the fluid absorption. It is worth mentioning though, that in vitro the fluid absorption was mainly governed by the expansion ability of the tampon, which was restricted by the net enclosure. Under in vivo conditions, however, the tampon is in a significantly more expanded form with the same fluid absorption volume.

2. Release Studies of Naproxen from Tampons Containing a Delivery System Attached to HDPE Substrates:

In an attempt to enhance the drug release kinetics, the formulated delivery system was attached to a thin film of high-density polyethylene (HDPE) which is a relatively inert and hydrophobic material, impermeable to water. The main concept of placing a thin HDPE substrate attached to the formulated chip was to facilitate the outward diffusion of the drug by minimizing the inward flow. The HDPE substrate was attached to the delivery system by sewing the edges with a cotton tread. The chip was mounted on the tampon with the HDPE substrate facing inward.

Figure 6A:
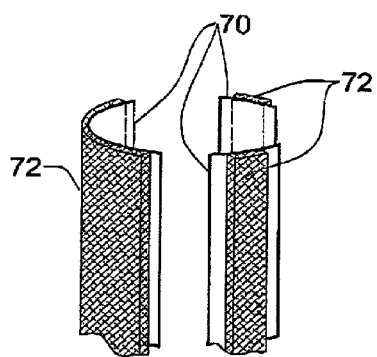
FIGS. 6a and 6b show embodiments of alternate structures of the delivery system with a polymeric film backing: a split arrangement (FIG. 6a) and a continuous arrangement (FIG. 6b)
Figure 6B:
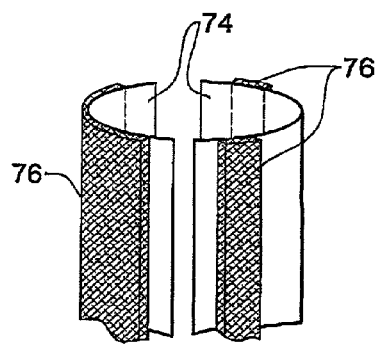

Two different approaches were tested. In one approach (type-A—FIG. 6a), a split HDPE substrate 70 was used, being only slightly larger than each of the formulated NW strips 72. In the second approach (type-B—FIG. 6b), a continuous substrate 74 was used covering almost the total area on each side of the tampon behind the formulated NW strips 76. A loose net enclosure was used, allowing a maximum fluid absorption of 10 ml.

3. Release Studies of Ibuprofen from Tampons in an Albumin-containing Release Medium Among the various parameters tested, it is the drug solubility and possibly its diffusion pattern that constitute the principle limiting factors in the drug release process. Thus, it was considered that the use of the Sorensen buffer alone as a release medium might not closely enough resemble the physicochemical properties of the menstrual fluid, in terms of drug dissolution.

Consequently, a plasma protein—albumin—was dissolved in the Sorensen buffer at a concentration of either 1% or 3%, the latter being the actual albumin concentration in the blood.

4. Measurement of Saturation Concentration—Determination of SINK Conditions:

An excess amount of drug (Ibuprofen) was added to 30 ml of Sorensen buffer (pH 7.4), containing either 1% or 3% of dissolved albumin, and agitated in sealed flasks at 37° C., for a period of 24h. The solution concentration was determined by HPLC.

The saturation concentrations obtained with the 1% and 3% albumin containing buffer solutions were approximately 730 μm/ml and 2100 μg/ml, respectively. These concentrations are respectively 7 to 21 times higher than the 100 μg/ml saturation concentration obtained with the Sorensen buffer alone. It is believed that either a complexation process between the protein and drug molecules, or a change in the solubility parameters of the solution led to such a significant increase in the drug saturation concentration.

SINK conditions were set at 6.8% and 14% for formulated tampons containing 50 mg and 100 mg of ibuprofen, respectively, in a volume of 1 liter of releasing medium containing 1% bovine serum albumin.

5. In vitro Drug Release Procedure:

The in vitro experimental conditions were set as follows: Drag release from formulated tampons was performed in a dissolution apparatus, consisting of 6 1-liter glass vessels immersed in a controlled temperature water bath and equipped with a controlled mechanical stirring system (130 rpm). Albumin concentration in the releasing medium was 1% and the solution was kept at a constant temperature of 37° C.

Formulated tampons were enclosed in a tight plastic net, restricting the maximum fluid absorption to 5–6 ml. The tampons were immersed into the releasing medium head down, held vertically by the string. A small glass weight was attached to the tampon, in order to prevent floating. All experiments were carried out in two replicas. Samples were taken in duplicates and treated as described in the previous section.

Following the release process, the tampons were washed with 50 ml of ethanol in order to extract the residual amounts of drug present in the tampon at the end of the process. The sum of the residual and the released amounts was considered as the total amount of drug originally present in the formulated tampon. The percent of drug release was thus calculated.

6. Release Studies Results:

Among the different formulations previously tested three versions were selected and compared under the new experimental conditions. These formulations differed in several parameters, i.e. the amount of drug per tampon, the type and amount of wetting agent, and the presence or absence of an HDPE substrate attached to the inner side of the formulated delivery system mounted on the tampons.

The selected formulations were as follows:

100 mg Ibuprofen*+25% glycerol; split HDPE substrate (a)

100 mg Ibuprofen*+10% Tween 80, split HDPE substrate (b)

100 mg Ibuprofen*+10% Tween 80; continuous HDPE substrate (c)

150 mg Ibuprofen*+20% glycerol+20% PEG 1000; no HDPE (d)

*amounts per tampon

Figure 7:
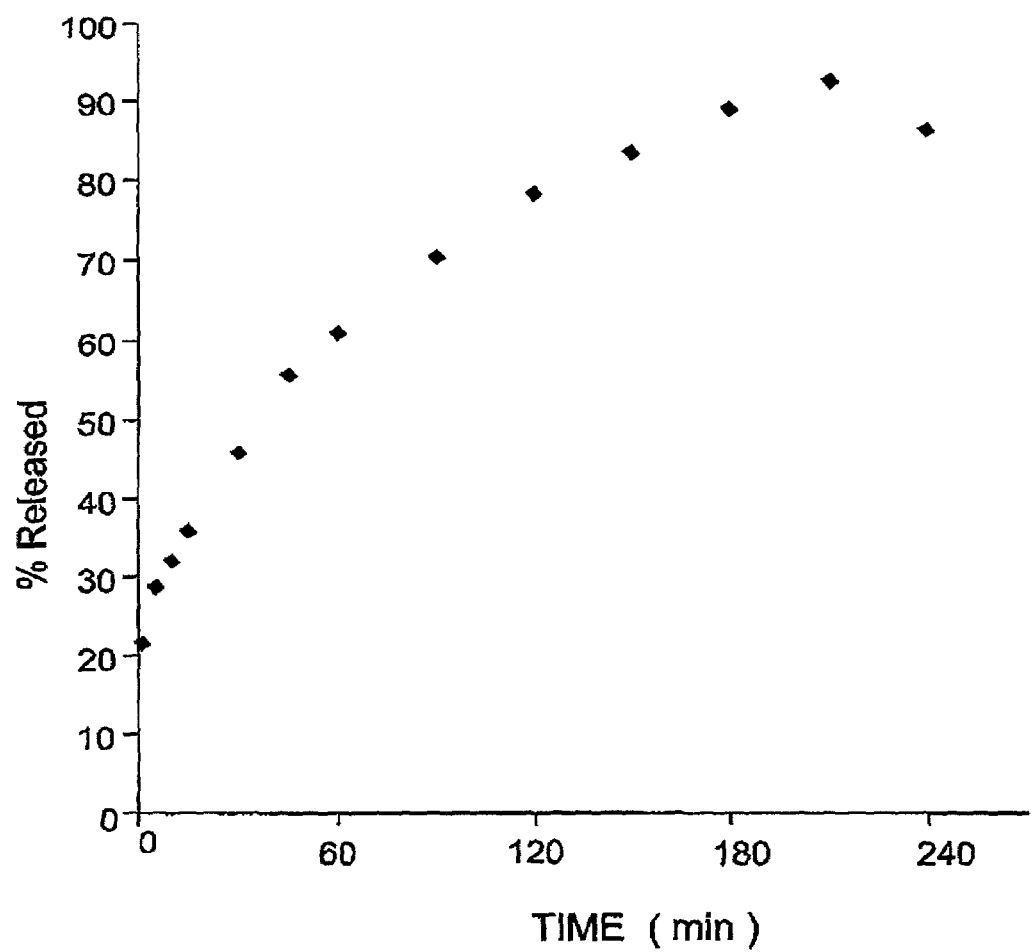
FIG. 7 shows release profiles of tampons, enclosed in a tight net, containing 100 mg of Ibuprofen and 25% glycerol with the delivery system attached to HDPE substrate type A (results of two replicas)
Figure 8:
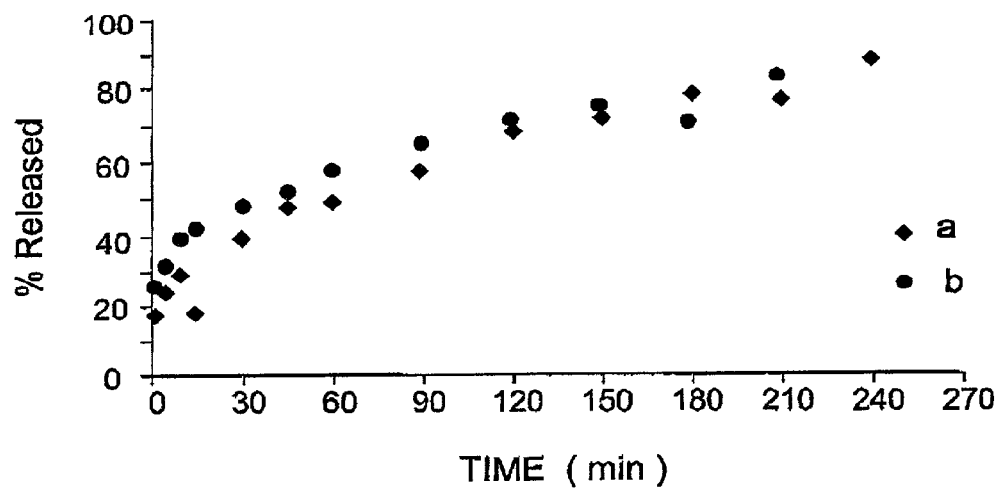
FIG. 8 shows release profiles of tampons, enclosed in a tight net, containing 100 mg of Ibuprofen and 10% Tween-80 with the delivery system attached to HDPE substrate type A (◆) and type B (●)
Figure 9:
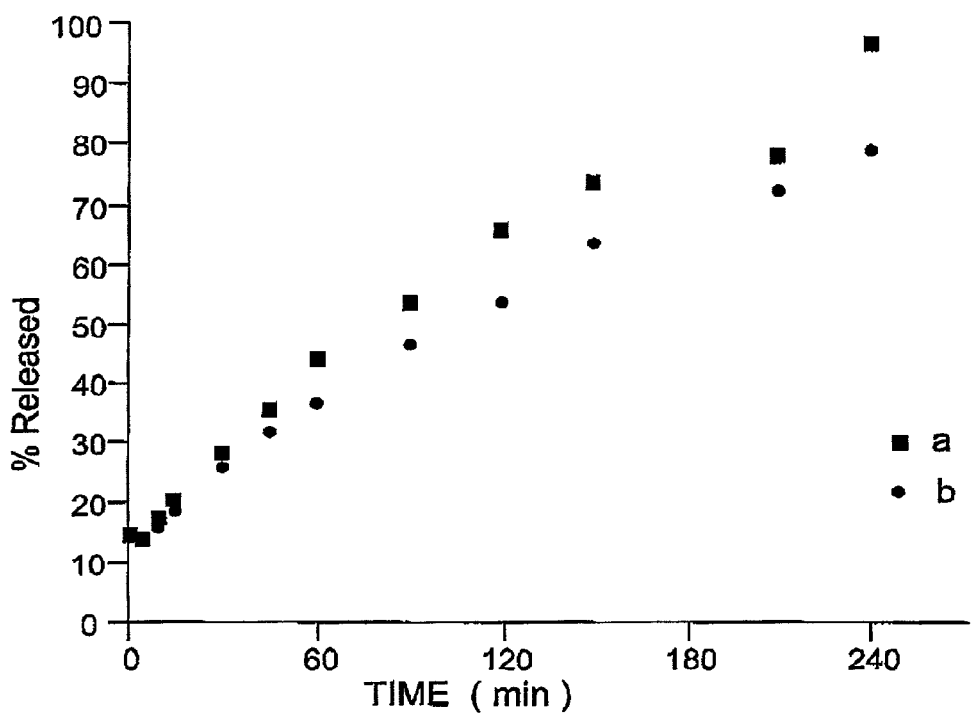
FIG. 9 shows release profiles of tampons, enclosed in a tight net, containing 150 mg of Ibuprofen, 20% glycerol and 20% PEG-900 (without HDPE substrates) (results of two replicas a (■) and b (●)).

The release profiles of the different formulated tampons, are presented in FIGS. 7, 8 and 9.

The release profile of formulation number (a), under tight net enclosure conditions, is depicted in FIG. 7. It can clearly be observed, that most of the formulation is released within the first 2 hours. The release profiles of formulation numbers (b) and (c), shown in FIG. 8 clearly indicate that the use of Tween 80 as wetting agent instead of glycerol, does not increase the release rate and even slows it down. No significant difference in the release profiles was observed when using either split or continuous HDPE substrates.

Finally, it can be noted from FIG. 9 that the release profile of the drug from a tampon including glycerol and PEG-1000 as wetting agents and no HDPE substrate (formulation (d)) was markedly reduced. Only 50–60% of the drug was released within 120 minutes, as compared to the approximately 80% of the drug which were released within the same period of time when using an HDPE substrate (FIG. 7), It is therefore suggested that the use of an HDPE substrate does promote and increase the rate of drug release.

What is claimed is:

1. A catamenial tampon for insertion in a human vagina comprising:
(a) an inner core comprising an absorbent material;
(b) an outer layer comprising a liquid-permeable material; and
(c) a transvaginal drug delivery system containing (i) a deposition having an effective amount of said drug and, optionally, a wetting agent; and (ii) a polymeric support on which said deposition is deposited, said polymeric support being in the form of a strip,
wherein said delivery system is positioned between said inner core and said outer layer.

2. A catamenial tampon according to claim 1 further comprising a polymeric water-impermeable film between said delivery system and said inner core.

3. A catamenial tampon according to claim 2 wherein said polymeric water-impermeable film comprises high-density polyethylene (HDPE).

4. A tampon according to claim 1 wherein said delivery system comprises a plurality of strips of the polymeric support.

5. A tampon according to claim 4 comprising 3 strips.

6. A method of transvaginal drug delivery comprising inserting a catamenial tampon into a vaginal wherein said catamenial tampon comprises:
(a) an inner core comprising an absorbent material;
(b) an outer layer comprising a liquid-permeable material; and
(c) a transvaginal drug delivery system containing (i) a deposition having an effective amount of said drug and, optionally, a wetting agent; and (ii) a polymeric support on which said deposition is deposited, wherein said polymeric support being in the form of a strip,
wherein said delivery system is positioned between said inner core and said outer layer.

7. A method according to claim 6 wherein said drug is a NSAID.

8. A method according to claim 7 wherein said NSAID is naproxen or ibuprofen.

* * * * *